(12) United States Patent
Zhang

(10) Patent No.: US 7,395,565 B2
(45) Date of Patent: Jul. 8, 2008

(54) PATIENT SUPPORTING APPARATUS AND MEDICAL IMAGE PHOTOGRAPHING APPARATUS

(75) Inventor: Jinglei Zhang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 448 days.

(21) Appl. No.: 11/265,986

(22) Filed: Nov. 3, 2005

(65) Prior Publication Data
US 2006/0090263 A1  May 4, 2006

(30) Foreign Application Priority Data
Nov. 4, 2004  (CN)  .................. 2004 1 0090364

(51) Int. Cl.
*A61G 13/12* (2006.01)
*A61B 6/04* (2006.01)

(52) U.S. Cl. .................. 5/623; 5/601; 5/600; 378/208; 378/205; 378/20; 248/425; 248/429

(58) Field of Classification Search ............ 5/601, 5/662, 600, 621, 623, 646; 378/204, 205, 378/208, 20; 248/419–425, 429
See application file for complete search history.

(56) References Cited

U.S. PATENT DOCUMENTS

| | | | |
|---|---|---|---|
| 5,181,289 A * | 1/1993 | Kassai | 5/612 |
| 5,433,222 A | 7/1995 | Boomgaarden et al. | |
| 5,590,429 A | 1/1997 | Boomgaarden et al. | |
| 5,597,146 A * | 1/1997 | Putman | 248/276.1 |
| 6,944,895 B2 * | 9/2005 | Truwit | 5/601 |
| 2002/0084761 A1 | 7/2002 | Zettel et al. | |
| 2003/0079287 A1 * | 5/2003 | Truwit | 5/601 |
| 2003/0202634 A1 | 10/2003 | Boomgaarden et al. | |
| 2006/0090263 A1 * | 5/2006 | Zhang | 5/662 |
| 2007/0277322 A1 * | 12/2007 | Pastusek | 5/662 |

* cited by examiner

*Primary Examiner*—Robert G Santos
(74) *Attorney, Agent, or Firm*—Armstrong Teasdale LLP

(57) ABSTRACT

With a view to attaining both easiness of position adjustment and sureness of position holding, a patient supporting apparatus comprises an arm for supporting a patient, the arm comprising a horizontal arm portion and a vertical arm portion, a rail for supporting the arm movably in a direction perpendicular to the horizontal arm portion and the vertical arm portion, and a brake for preventing movement of the arm along the rail by utilizing a moment of rotation with the vertical arm portion of the arm being as an axis.

16 Claims, 6 Drawing Sheets

PATIENT SUPPORTING APPARATUS AND MEDICAL IMAGE PHOTOGRAPHING APPARATUS

CROSS REFERENCE TO RELATED APPLICATIONS

This application claims the benefit of Chinese Application No. 200410090364.X filed Nov. 4, 2004.

BACKGROUND OF THE INVENTION

The present invention relates to a patient supporting apparatus and a medical image photographing apparatus. Particularly, the present invention is concerned with an apparatus for supporting a patient during medical image photographing and a medical image photographing apparatus having the patient supporting apparatus.

When the body of a patient is photographed sideways by means of an X-ray photographing apparatus, the photographing is performed with both arms of the patient raised. For supporting both arms of the patient there is a need to use a supporting apparatus. The supporting apparatus is provided with a vertical arm portion mounted on the back side of an X-ray receiving panel and a horizontal arm portion projecting toward the patient side from an upper end of the vertical arm portion. The horizontal arm portion is convenient for the patient to grasp with both hands. A vertical arm mounting mechanism results in that the position of the vertical arm can be adjusted in a stepless manner in a direction parallel to the X-ray receiving panel (see, for example, Patent Literature 1).

[Patent Literature 1] U.S. Patent Application Laid Open No. 2003/0202635 (pp. 4-5, FIG. 8)

For the vertical arm mounting mechanism in the above patient supporting apparatus it is required that the position of the vertical arm be easily adjustable and that an accurately adjusted position be able to be held positively. However, both requirements are generally difficult to be satisfied at the same time. More particularly speaking, if the position adjustment is made easier, the vertical arm becomes easier to be moved by the patient during photographing, while if the vertical arm portion is made difficult to be moved, it will become difficult to effect position adjustment.

SUMMARY OF THE INVENTION

Therefore, it is an object of the present invention to provide a patient supporting apparatus capable of realizing both easiness of position adjustment and sureness of position holding and also provide a medical image photographing apparatus having such a patient supporting apparatus.

(1) In one aspect of the present invention, for solving the above-mentioned problem, there is provided a patient supporting apparatus comprising an arm for supporting a patient, the arm comprising a horizontal arm portion and a vertical arm portion; a rail for supporting the arm movably in a direction perpendicular to the horizontal arm portion and the vertical arm portion; and a brake for preventing movement of the arm along the rail by utilizing a moment of rotation with the vertical arm portion of the arm being as an axis.

(2) In another aspect of the present invention, for solving the above-mentioned problem, there is provided a medical image photographing apparatus comprising a patient supporting means and a photographing means for photographing a medical image of a patient supported by the patient supporting means, the patient supporting means comprising an arm supporting a patient and comprising a horizontal arm portion and a vertical arm portion; a rail for supporting the arm movably in a direction perpendicular to the horizontal arm portion and the vertical arm portion; and a brake for preventing movement of the arm along the rail by utilizing a moment of rotation centered on the vertical arm portion of the arm.

For the simplification of construction it is preferable that the brake be provided with a sub-rail parallel to the rail and a brake shoe adapted to be pressed against the sub-rail by utilizing the moment of rotation.

For simplifying the structure of the brake shoe it is preferable that the sub-rail be a grooved rail. Further, it is preferable for the brake shoe to have a fitting portion for fitting in the groove of the sub-rail. This is preferable because braking is applied the brake by utilizing friction induced between the fitting portion and an inner wall of the groove.

It is preferable that there is a driven gear on the brake shoe, a rotating force based on the moment of rotation is imparted to the driven gear. Therefore, this is preferable because the moment of rotation is transferred effectively. For the same reason it is preferable that there is a driven gear on the vertical arm portion of the arm, for imparting the rotating force to the driven gear.

For supporting a patient properly it is preferable that the horizontal arm portion of the arm be for the patient to grasp. It is preferable that the horizontal arm portion of the arm be for the patient to grasp with his or her arms raised. This is preferable for preventing the patient's arms from blocking the X-ray within the photographing visual field.

According to the present invention in the above aspects, the patient supporting apparatus comprises an arm for supporting a patient, the arm comprising a horizontal arm portion and a vertical arm portion; a rail for supporting the arm movably in a direction perpendicular to the horizontal arm portion and the vertical arm portion; and a brake for preventing movement of the arm along the rail by utilizing a moment of rotation centered on the vertical arm portion of the arm. With this construction, when the apparatus supports a patient, a brake is applied the brake by a moment of rotation which acts on the vertical arm portion through the horizontal arm portion, whereby the sureness of the position holding is ensured, while when the apparatus does not support a patient, a brake is not applied the brake and the vertical arm portion can be moved easily along the rail. Thus, it is possible for the patient supporting apparatus to realize the functions that both easiness of position adjustment and sureness of position holding, and a medical image photographing apparatus having such a patient supporting apparatus.

Further objects and advantages of the present invention will be apparent from the following description of the preferred embodiments of the invention as illustrated in the accompanying drawings.

DETAILED DESCRIPTION OF THE INVENTION

Figure 1:
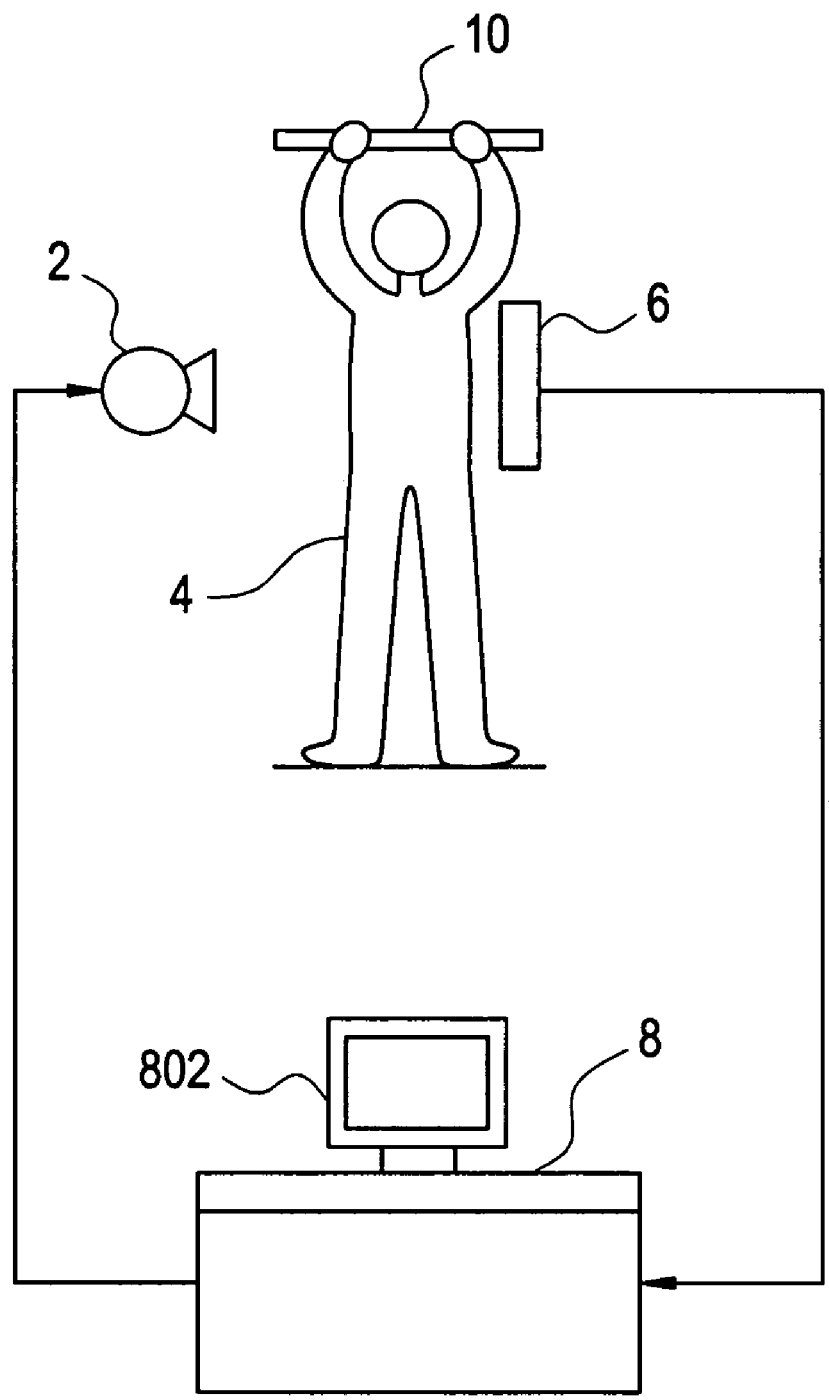
FIG. 1 illustrates a medical image photographing apparatus according to an example of the best mode for carrying out the present invention.

A best mode for carrying out the present invention will be described below with reference to the accompanying drawings, provided the invention is not limited to the best mode. FIG. 1 shows the construction of an X-ray photographing apparatus which is an example of the best mode for carrying out the invention. With the construction of this apparatus, there is shown an example of the best mode for carrying out the invention related to the medical image photographing apparatus.

In the X-ray photographing apparatus, as shown in the same one figure, X-ray is radiated from an X-ray tube 2 to a patient 4, then transmitted X-ray is received by an X-ray receiving panel 6, and a received light signal is processed by a photographing console 8 to reconstruct a perspective image of the patient 4. The reconstructed perspective image is displayed on a display 802 of the photographing console 8. The portion comprising the X-ray tube 2, X-ray receiving panel 6 and photographing console 8 is an example of the photographing means defined in the present invention The patient 4 stands up sideways of the X-ray receiving panel 6 and X-ray is radiated sideways of the patent. The patient assumes a posture that both arms are raised to grasp a patient supporting apparatus 10 located above the head of the patient and to thereby prevent both arms from being present within a visual field for photographing. The patient supporting apparatus 10 is an example of the patient supporting means defined in the present invention.

Figure 2:
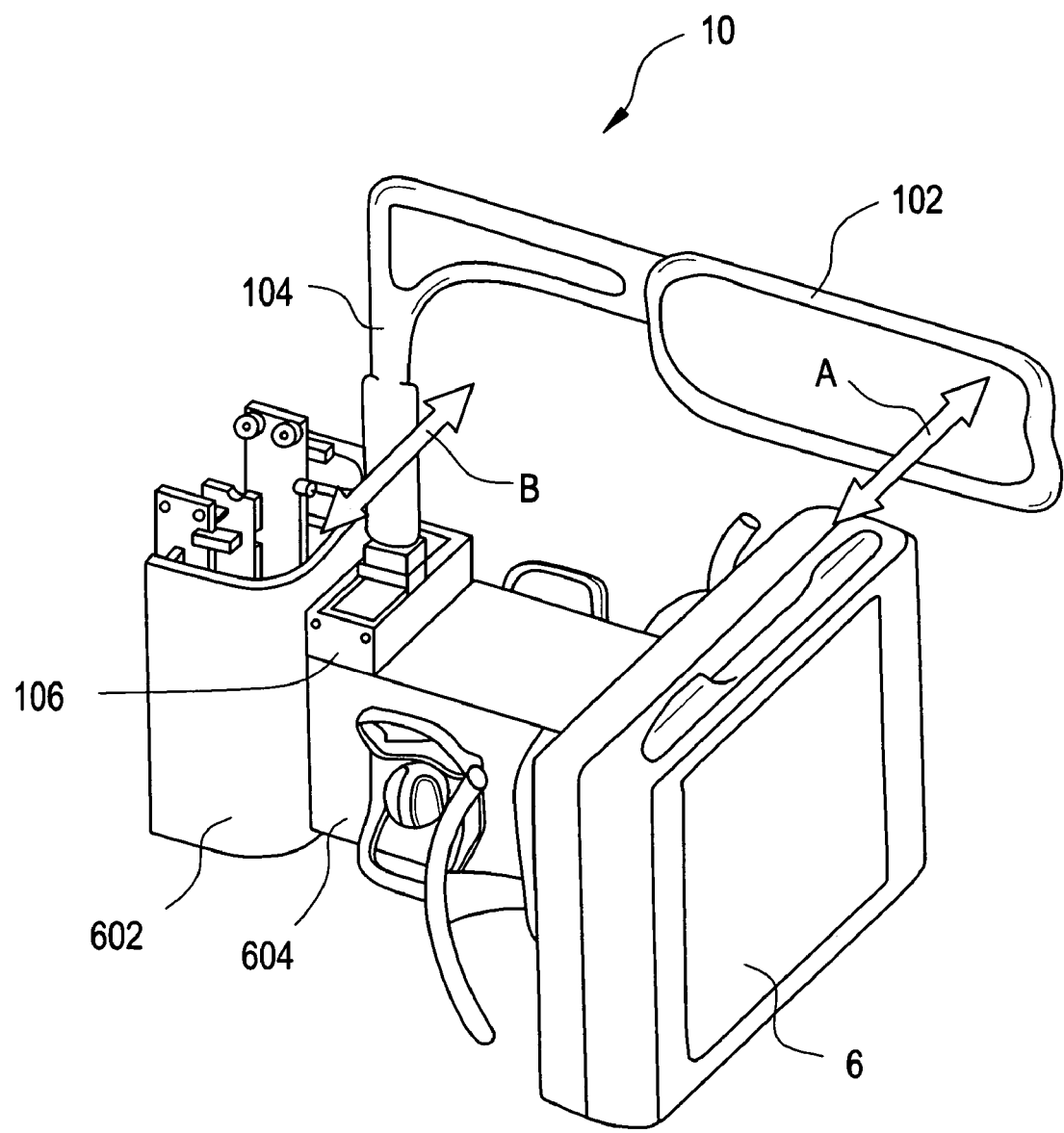
FIG. 2 illustrates a patient supporting apparatus according to another example of the best mode for carrying out the present invention.

FIG. 2 is a perspective view showing the construction of the patient supporting apparatus 10, together with the X-ray receiving panel 6. The patient supporting apparatus 10 is an example of the best mode for carrying out the present invention. With the construction of this apparatus, there is shown an example of the best mode for carrying out the invention related to the patient supporting apparatus.

As shown in the same figure, a rear side of the X-ray receiving panel 6 is mounted on a front end of a cross beam 604 which extends from a support post 602. A front side of the X-ray receiving panel 6 confronts a patient. The patient supporting apparatus 10 is mounted on the end portion of the cross beam 604 which is located on the side opposite to the panel 6.

The patient supporting apparatus 10 has a generally L-shaped arm comprising a horizontal arm portion 102 and a vertical arm portion 104. The horizontal arm portion 102 extends from an upper end of the vertical arm portion 104, passes over the X-ray receiving panel 6 and projects to the front side of the panel 6. A base portion of the vertical arm portion 104 is supported by a base assembly 106. The L-shaped arm comprising the horizontal arm portion 102 and the vertical arm portion 104 is an example of the arm in the present invention. The horizontal arm portion 102 is an example of the horizontal arm portion defined in the present invention and the vertical arm portion 104 is an example of the vertical arm portion defined in the present invention.

Figure 3:
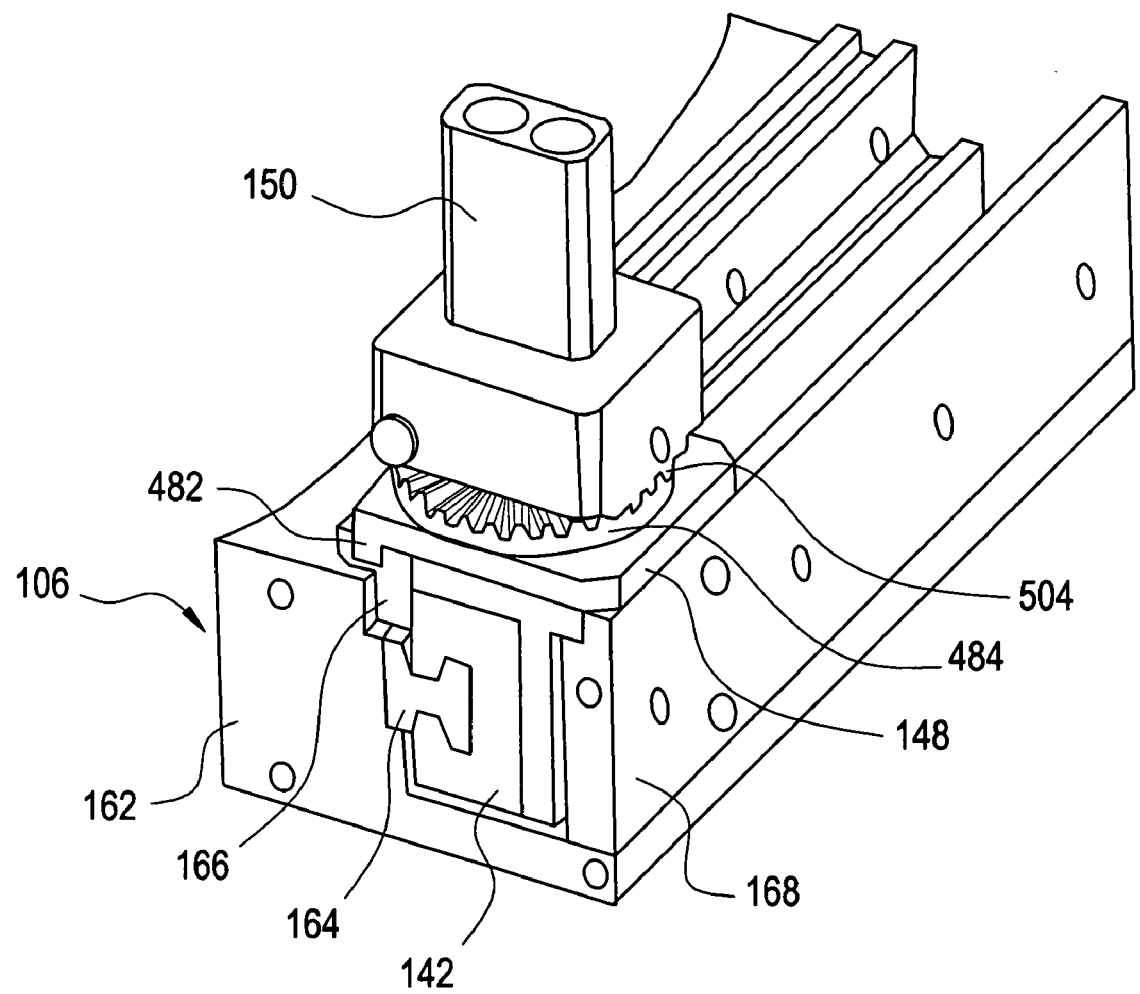
FIG. 3 is a perspective view showing a partial construction of the patient supporting apparatus.
Figure 4:
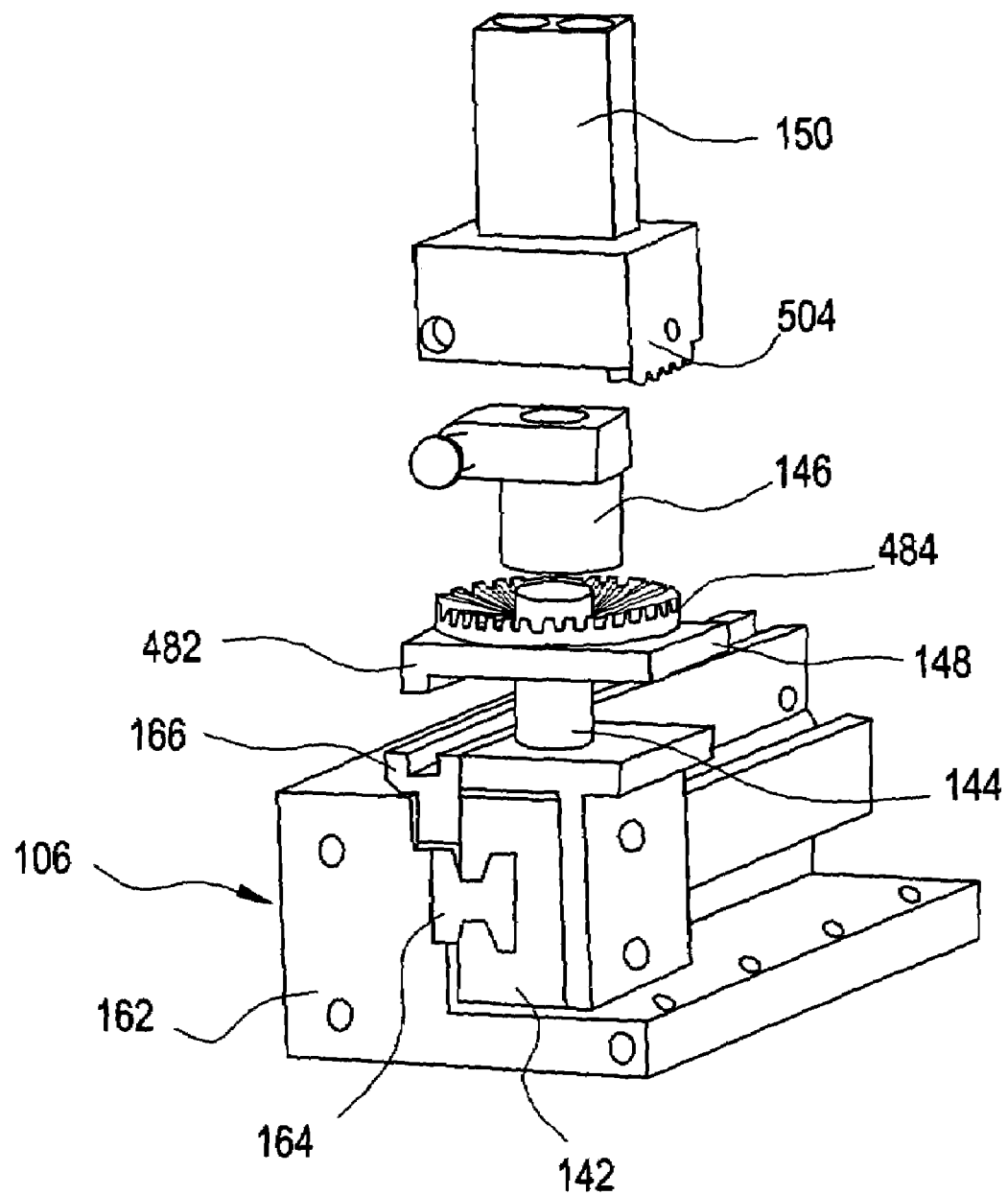
FIG. 4 is an exploded view showing a partial construction of the patient supporting apparatus.
Figure 5:
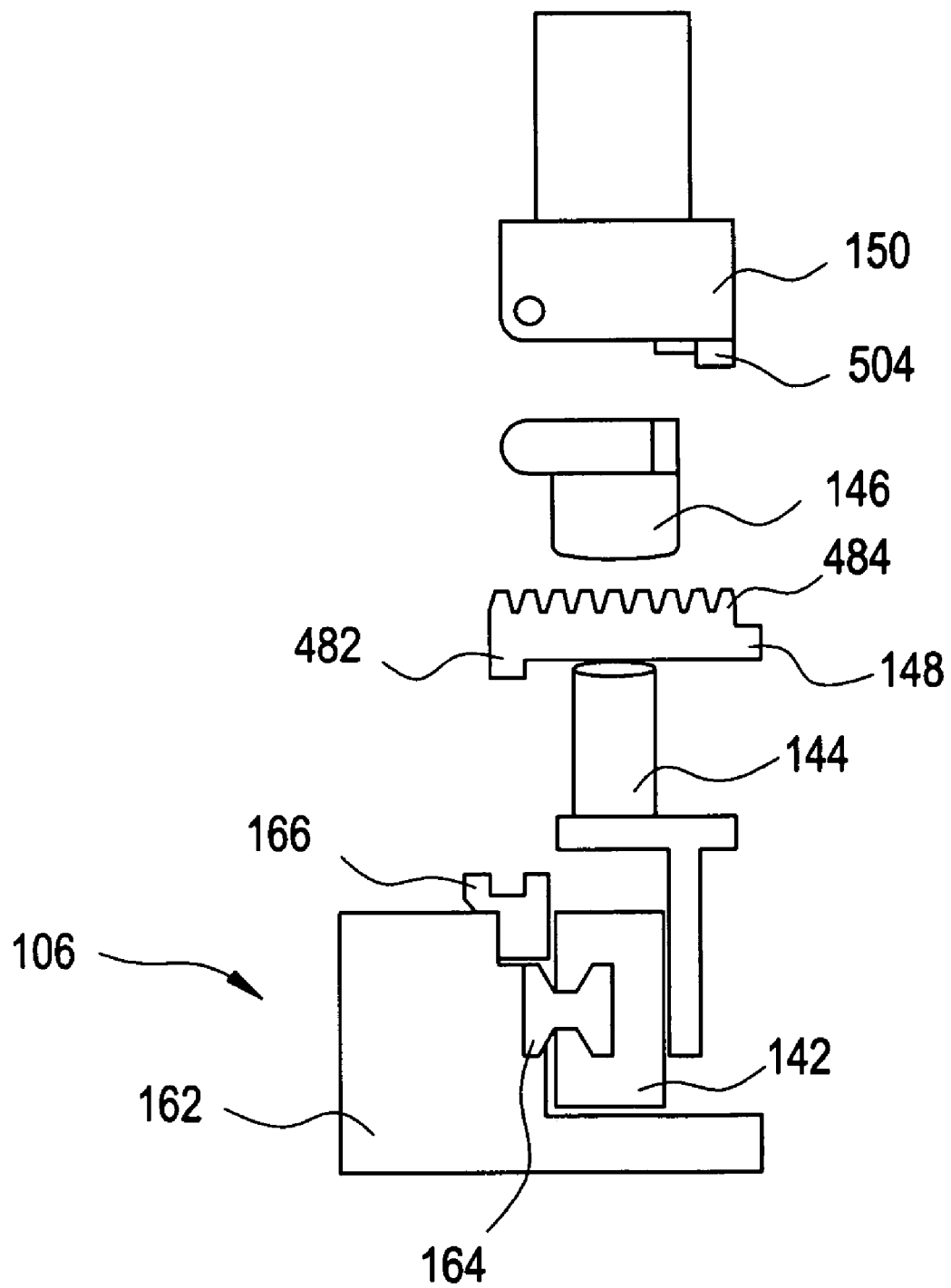
FIG. 5 is an exploded view showing a partial construction of the patient supporting apparatus.
Figure 6:
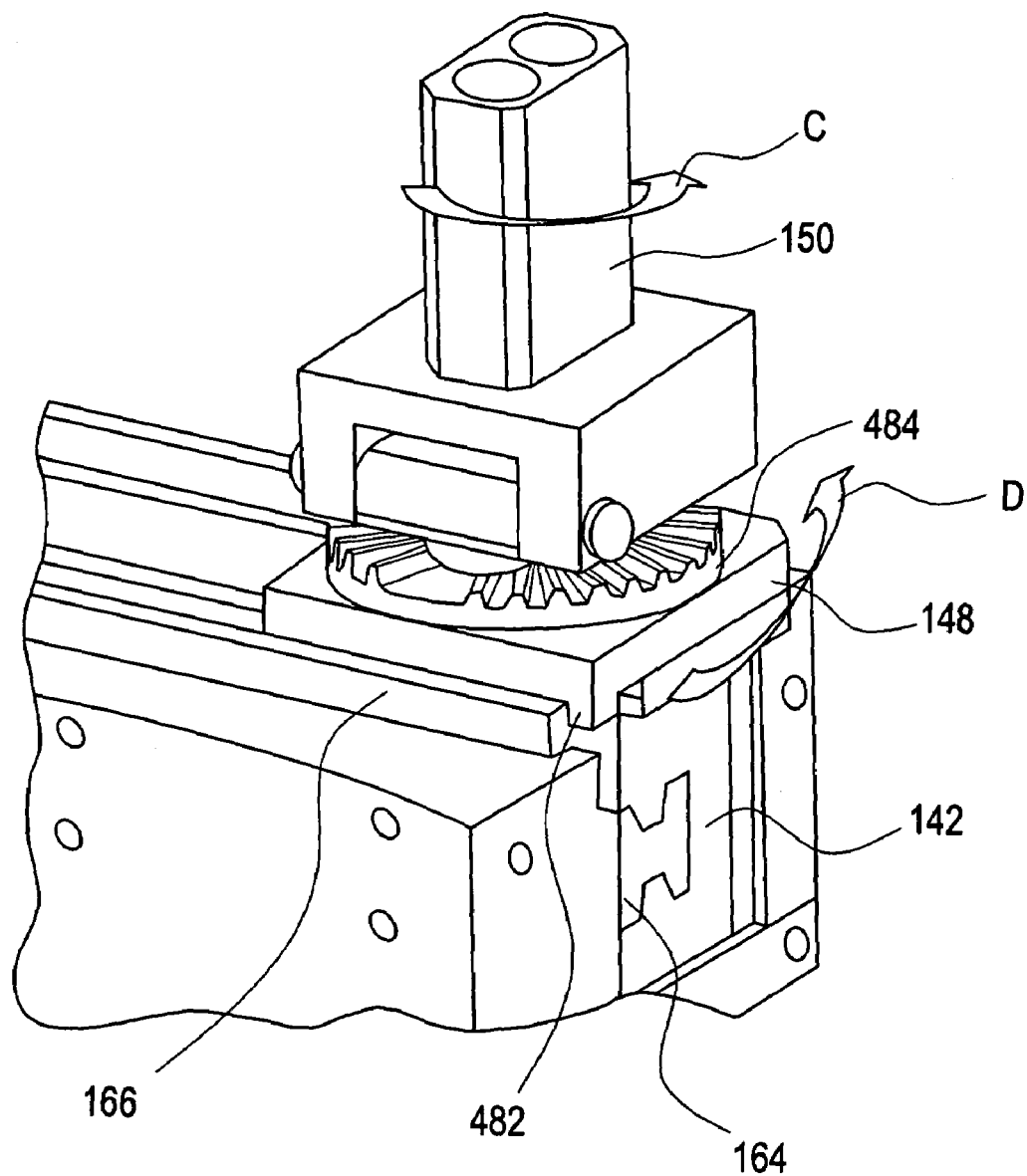
FIG. 6 is a perspective view showing a partial construction of the patient supporting apparatus.

FIGS. 3 to 6 show the structure of the base portion of the vertical arm portion 104 and that of the base assembly 106, of which FIG. 3 is a perspective view from a front side, FIGS. 4 and 5 are partially cut-away exploded views, and FIG. 6 is a perspective view from a rear side.

As shown in these figures, the base assembly 106 includes a base member 162, a main rail 164 and a sub-rail 166 both secured to the base member 162, and a front plate 168. The main rail 164, the sub-rail 166 and the front plate 168 are parallel to one another and have a longitudinal direction perpendicular to the horizontal arm portion 102 and the vertical arm portion 104. The main rail 164 is an example of the rail defined in the present invention.

The main rail 164 has an H-shaped section and one side face thereof is secured to the base member 162. The sub-rail 166 has a groove formed in an upper surface thereof and is secured to the base member 162 so that the groove faces up. The front plate 168 serves as a bumper plate for the base assembly 106.

The base portion of the vertical arm portion 104 includes a slider 142 engaged with the main rail 164, a main shaft 144 mounted to the slider 142, a collar 146 fitted loosely on the main shaft, a brake shoe 148 fitted loosely on the collar 146, and a stud 150 mounted on the collar 146. The vertical arm portion 104 is secured to the stud 150.

The main shaft 144 is a central shaft of the vertical arm portion 104 and extends vertically. The collar 146, the brake shoe 148 and the stud 150 are coaxial with the main shaft 144. The brake shoe 148 has an L-shaped fitting portion 482 for fitting in the groove of the sub-rail 166. The brake shoe 148 also has a gear 484 on an upper surface thereof. The gear 484 is in mesh with a gear 504 mounted on a lower surface of the stud 150.

Since the base portion of the vertical arm portion 104 and the base assembly 106 have such structures, when the horizontal arm 102 is pushed or pulled in the horizontal direction as indicated with arrow A as shown in FIG. 2, a moment of rotation with the axis of the vertical arm 104 being as a center acts on the vertical arm portion.

This moment of rotation, which is indicated with arrow C in FIG. 6, is transmitted as such a moment of rotation as indicated with arrow D to the brake shoe 148 through the engagement between the gear 504 on the lower surface of the stud 150 and the gear 484 on the upper surface of the brake shoe 148.

With such a moment of rotation, a side face of the fitting portion 482 of the brake shoe 148 is pressed against a side face of the groove within the sub-rail 166, resulting in that a frictional force between the two increases. Since this increase in frictional force inhibits movement of the slider 142, the vertical arm portion 104 cannot move.

A pulling force of a pushing force acts in arrow A direction on the horizontal arm portion 102 when the patient grasps the horizontal arm 102. However, in such a case, movement of the vertical arm portion 104 is inhibited as above and the patient supporting apparatus 10 is sure to be held in position.

The portion comprising the sub-rail 166 and the brake shoe 148 is an example of the brake defined in the present invention. The sub-rail 166 is an example of the sub-rail defined in the present invention. The brake shoe 148 is an example of the brake shoe defined in the present invention.

The gear 504 is an example of the drive gear defined in the present invention. The gear 484 is an example of the driven gear defined in the present invention.

Since the brake includes the sub-rail 166 parallel to the main rail 164 and the brake shoe 148 adapted to be pushed against the sub-rail by utilizing a moment of rotation, it is possible to simplify its construction.

Since the sub-rail 166 is a grooved rail, it is possible to simplify the structure of the brake shoe. Since the brake shoe 148 has the fitting portion 482 for fitting in the groove of the sub-rail 166, it is possible to apply the brake by utilizing friction inducted between the fitting portion and the inner wall of the groove.

Since the brake shoe 148 has the driven gear 484 onto which a rotating force generated by a moment of rotation is imparted, it is possible to receive the moment of rotation effectively. Since the stud 150 with the vertical arm portion 104 secured thereto is provided with the drive gear 504 which imparts the rotating force to the driven gear 484, it is possible to enable the rotational moment to be transferred effectively.

Since the horizontal arm portion 102 is for a patient to grasp, it is possible to support the patient properly. Further, since the horizontal arm portion 102 is for to be grasped by the patient's raised arms, it is possible to prevent the arms from being present within the visual field for photographing.

For changing the position of the patient supporting apparatus 10, a horizontal force is applied to the vertical arm portion 104 as indicated with arrow B in FIG. 2. At this time, a moment of rotation centered on the vertical arm portion 104 is not generated, therefore a braking force can not be generated by the brake shoe 148. Consequently, the slider 142 can be moved smoothly and hence it is easy to adjust the patient supporting apparatus 10.

Many widely different embodiments of the invention may be configured without departing from the spirit and the scope of the present invention. It should be understood that the present invention is not limited to the specific embodiments described in the specification, except as defined in the appended claims.

The invention claimed is:

1. A patient supporting apparatus comprising:
   an arm for supporting a patient, the arm comprising a horizontal arm portion and a vertical arm portion;
   a rail for supporting the arm movably in a direction perpendicular to the horizontal arm portion and the vertical arm portion; and
   a brake for preventing movement of the arm along the rail by utilizing a moment of rotation with the vertical arm portion of the arm being as an axis.

2. A patient supporting apparatus according to claim 1, wherein the brake comprises:
   a sub-rail parallel to the rail; and
   a brake shoe adapted to be pressed against the sub-rail by utilizing the moment of rotation.

3. A patient supporting apparatus according to claim 2, wherein the sub-rail is a grooved rail.

4. A patient supporting apparatus according to claim 3, wherein the brake shoe has a fitting portion for fitting in the groove of the sub-rail.

5. A patient supporting apparatus according to claim 2, wherein the brake shoe has a driven gear to which a rotating force based on the moment of rotation is imparted.

6. A patient supporting apparatus according to claim 5, wherein the vertical arm portion of the arm imparts the rotating force to the driven gear.

7. A patient supporting apparatus according to claim 1, wherein the horizontal arm portion of the arm is for the patient to grasp.

8. A patient supporting apparatus according to claim 7, wherein the horizontal arm portion of the arm is for the patient to grasp with his or her arms up.

9. A medical image photographing apparatus comprising a patient supporting unit and a photographing unit for photographing a medical image of a patient supported by the patient supporting unit, the patient supporting unit comprising:
   an arm for supporting a patient, the arm comprising a horizontal arm portion and a vertical arm portion;
   a rail for supporting the arm movably in a direction perpendicular to the horizontal arm portion and the vertical arm portion; and
   a brake for preventing movement of the arm along the rail by utilizing a moment of rotation with the vertical arm portion of the arm being as an axis.

10. A medical image photographing apparatus according to claim 9, wherein the brake comprises:
    a sub-rail parallel to the rail; and
    a brake shoe adapted to be pushed against the rail by utilizing the moment of rotation.

11. A medical image photographing apparatus according to claim 10, wherein the sub-rail is a grooved rail.

12. A medical image photographing apparatus according to claim 11, wherein the brake shoe has a fitting portion for fitting in the groove of the sub-rail.

13. A medical image photographing apparatus according to any of claim 10, wherein the brake shoe has a driven gear to which a rotating force based on the moment of rotation is imparted.

14. A medical image photographing apparatus according to claim 13, wherein the vertical arm portion of the arm has a drive gear for imparting a rotating force to the driven gear.

15. A medical image photographing apparatus according to claim 9, wherein the horizontal arm portion of the arm is for the patient to grasp.

16. A medical image photographing apparatus according to claim 15, wherein the horizontal arm portion of the arm is for the patient to grasp with his or her arms up.

* * * * *